United States Patent
Su

(10) Patent No.: US 6,421,457 B1
(45) Date of Patent: Jul. 16, 2002

(54) PROCESS INSPECTION USING FULL AND SEGMENT WAVEFORM MATCHING

(75) Inventor: Bo Su, San Jose, CA (US)

(73) Assignee: Applied Materials, Inc., Santa Clara, CA (US)

(*) Notice: Subject to any disclaimer, the term of this patent is extended or adjusted under 35 U.S.C. 154(b) by 0 days.

(21) Appl. No.: 09/249,938

(22) Filed: Feb. 12, 1999

(51) Int. Cl.[7] .............................. G06K 9/00; H04N 7/18; G01N 21/00; G03F 9/00
(52) U.S. Cl. ...................... 382/149; 348/87; 356/237.4; 430/22
(58) Field of Search .................................. 382/145, 146, 382/147, 149; 348/86, 87, 125, 126, 129; 356/237.4, 237.5; 430/22, 30

(56) References Cited

U.S. PATENT DOCUMENTS

| | | | | |
|---|---|---|---|---|
| 5,325,309 A | * | 6/1994 | Halaviati et al. | 703/15 |
| 5,876,883 A | * | 3/1999 | Leroux | 430/22 |
| 5,960,107 A | * | 9/1999 | Leroux | 382/145 |
| 6,018,391 A | * | 1/2000 | Yoshida | 356/484 |
| 6,172,365 B1 | * | 1/2001 | Hiroi et al. | 250/310 |
| 6,178,257 B1 | * | 1/2001 | Alumot et al. | 382/145 |
| 6,185,323 B1 | * | 2/2001 | Archie et al. | 382/145 |

* cited by examiner

Primary Examiner—Amelia M. Au
Assistant Examiner—Mehrdad Dastouri
(74) Attorney, Agent, or Firm—McDermott, Will & Emery LLP.

(57) ABSTRACT

A method and apparatus for inspecting a feature formed on the surface of a semiconductor wafer predicts the profile of the feature and pinpoints the stepper settings of the inspected feature by inspecting the feature using standard SEM imaging techniques. Embodiments include forming and SEM-imaging a plurality of reference features, comparable to the target feature to be inspected, on a reference semiconductor wafer, each of the reference features associated with a known profile and stepper setting. The reference SEM waveform associated with an optimal profile is selected as a golden waveform, then a waveform corresponding to the target feature is compared with the golden waveform. If the target waveform does not substantially match the golden waveform, the reference waveform which most closely matches the target waveform is identified, to determine the profile and stepper settings of the target feature. The difference between the golden waveform stepper setting and the target feature stepper setting is then determined. Thus, the profile and stepper settings of the inspected feature are pinpointed, thereby facilitating investigation of the causes of feature defects or variations from optimal dimensions and enabling effective corrective action to be implemented.

31 Claims, 7 Drawing Sheets

PROCESS INSPECTION USING FULL AND SEGMENT WAVEFORM MATCHING

FIELD OF THE INVENTION

The present invention relates to a method for monitoring photolithographic processing carried out on a semiconductor substrate, and more particularly for inspecting the cross-sectional profile of a feature formed on the semiconductor substrate. The invention has particular applicability for in line inspection of semiconductor wafers during manufacture of high-density semiconductor devices with submicron design features.

BACKGROUND ART

Current demands for high density and performance associated with ultra large scale integration require submicron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

One important process requiring careful inspection is photolithography, wherein masks are used to transfer circuitry patterns to semiconductor wafers. Typically, a series of such masks are employed in a preset sequence. Each photolithographic mask includes an intricate set of geometric patterns corresponding to the circuit components to be integrated onto the wafer. Each mask in the series is used to transfer its corresponding pattern onto a photosensitive layer (i.e., a photoresist layer) which has been previously coated on a layer, such as a polysilicon or metal layer, formed on the silicon wafer. The transfer of the mask pattern onto the photoresist layer is conventionally performed by an optical exposure tool such as a scanner or a stepper, which directs light or other radiation through the mask to expose the photoresist. The photoresist is thereafter developed to form a photoresist mask, and the underlying polysilicon or metal layer is selectively etched in accordance with the mask to form features such as lines or gates.

Fabrication of the mask follows a set of predetermined design rules set by processing and design limitations. These design rules define, e.g., the space tolerance between devices and interconnecting lines and the width of the lines themselves, to ensure that the devices or lines do not overlap or interact with one another in undesirable ways. The design rule limitation is referred to as the critical dimension ("CD"), defined as the smallest width of a line or the smallest space between two lines permitted in the fabrication of the device. The CD for most ultra large scale integration applications is on the order of a fraction of a micron.

As design rules shrink and process windows (i.e., the margins for error in processing) become smaller, inspection and measurement of surface features cross-sectional shape ("profile"), as well as CD, is becoming increasingly important. Deviations of a feature's profile from design dimensions may adversely affect the performance of the finished semiconductor device. Furthermore, the measurement of a feature's profile is sometimes as important, or more important, than the measurement of its CD, since the profile may indicate processing problems, such as stepper defocusing or photoresist loss due to cover-exposure, not readily revealed by CD information.

For example, FIG. 1A shows an ideal profile 100 (i.e., the profile intended by the designer) of a typical feature on the surface of a semiconductor wafer, and FIG. 1B shows a typical actual profile 100a of the same feature. Although the ideal profile 100 and the actual profile 100a are significantly different, they both have the same CD. As graphically depicted in FIG. 2, a feature's profile can be more sensitive to photolithographic process parameters, such as stepper focusing and exposure, than the feature's CD. In other words, as the stepper's parameters change, a feature's CD may not change significantly, but its profile may change dramatically.

Because of the extremely small scale of current CD's, the instrument of choice for measurement and inspection of surface features produced by photolithographic processing is a scanning electron microscope (SEM) known as a "critical dimension scanning electron microscope" (CD-SEM). However, although SEM's are useful for measuring CD's, they do not provide an adequately detailed direct image or measurement of feature profiles. Consequently, conventional techniques for inspecting profiles include sectioning the wafer and measuring feature profiles, as with a dual-beam system such as a focused ion beam scanning electron microscope (FIB-SEM). Another profile inspection technique involves the use of an atomic force microscope to examine surface features without destroying the wafer under test. However, these techniques are disadvantageous in that they are inherently time-consuming engineering and analysis tools rather than inspection tools, and must be used "off-line" in a yield laboratory. Thus, they do not provide information in "real time", when it would be most useful for monitoring process quality and implementing early solutions to processing problems.

Furthermore, none of the conventional techniques provide information relating to the cause of any profile or CD defects they may uncover. When the measured CD or profile is found to be outside a pre-designated dimensional range, it signifies that something is wrong with the stepper. However, it is not known from the CD or profile measurement whether; e.g., it is the stepper focus or exposure or both that is out of limits. Consequently, further tests must be performed to determine the cause of the problem, adding to the time and cost of inspection.

There exists a need for a simple, cost-effective methodology for in-process inspection of semiconductor wafers to provide information relating to feature CD and profile, as well as information relating to the photolithography process.

SUMMARY OF THE INVENTION

An advantage of the present invention is the ability to perform in-process inspection of features on a semiconductor substrate using a standard CD-SEM, providing information relating to the CD and profile characteristics of the features, and identifying process problem areas.

According to the present invention, the foregoing and other advantages are achieved in part by a method of inspecting a target feature on a semiconductor wafer, which method comprises forming a plurality of comparable reference features on a reference semiconductor wafer, the reference features having a profile comparable to a profile of the target feature, each of the reference features respectively associated with a different known profile and stepper setting; obtaining a reference waveform of each of the reference features; selecting one of the reference waveforms as a golden waveform; obtaining a target waveform of the target feature; comparing the target waveform with the golden waveform; identifying the reference waveform which most closely matches the target waveform to obtain the profile of the target feature and a target feature stepper setting; and determining the difference between the stepper setting associated with the golden waveform and the stepper setting associated with the target feature when the golden waveform is not the reference waveform that most closely matches the target waveform.

In another aspect of the present invention, if it is determined that the target waveform does not match the golden waveform, the step of identifying the reference waveform which most closely matches the target waveform comprises obtaining a first derivative of the target and reference waveforms; dividing the first derivative of the target waveform and the derivatives of the reference waveforms into at least two segments; separately comparing corresponding segments of the derivatives of the target waveform and the reference waveforms to identify which segments of the derivatives of the reference waveforms most closely match the corresponding segments of the derivative of the target waveform; and assembling the profiles associated with the matching segments of the derivatives of the reference waveforms to predict the profile of the target feature.

A further aspect of the present invention is a computer-readable medium bearing instructions for inspecting a target feature on a semiconductor wafer, said instructions, when executed, being arranged to cause one or more processors to perform the steps of receiving a waveform corresponding to the target feature; receiving a plurality of reference waveforms corresponding to a plurality of comparable reference features on a reference semiconductor wafer, the reference features having a profile comparable to a profile of the target feature, each of the reference features respectively associated with a different known profile and stepper setting; receiving one of the reference waveforms as a golden waveform; comparing the target waveform and the golden waveform; identifying the reference waveform which most closely matches the target waveform to obtain the profile of the target feature and a target feature stepper setting; and determining the difference between the stepper setting associated with the golden waveform and the stepper setting associated with the target feature when the golden waveform is not the reference waveform that most closely matches the target waveform.

A still further aspect of the present invention is an apparatus for inspecting a target feature on a semiconductor wafer, the apparatus comprising an imager to produce a target waveform corresponding to the target feature; a storage medium that stores the target waveform and a plurality of reference waveforms corresponding to a plurality of comparable reference features on a reference semiconductor wafer, the reference features having a profile comparable to a profile of the target feature, each of the reference features respectively associated with a different known profile and stepper setting; a processor configured to recognize one of the reference waveforms as a golden waveform; and a comparator that compares the target waveform and the golden waveform, and compares the target waveform and the reference waveforms; wherein the processor is further configured to identify the reference waveform which most closely matches the target waveform to obtain the profile of the target feature and a target feature stepper setting, and to determine the difference between the stepper setting associated with the golden waveform and the stepper setting associated with the target feature when the golden waveform is not the reference waveform that most closely matches the target waveform.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the present invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Figure 1A:
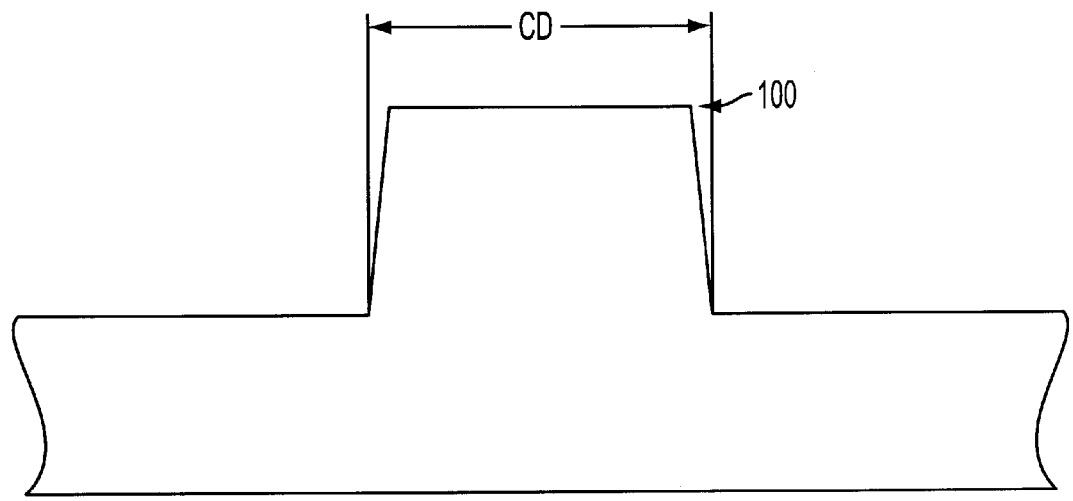
FIGS. 1A–1B are views of ideal and actual profiles of a feature formed on a semiconductor wafer.
Figure 1B:
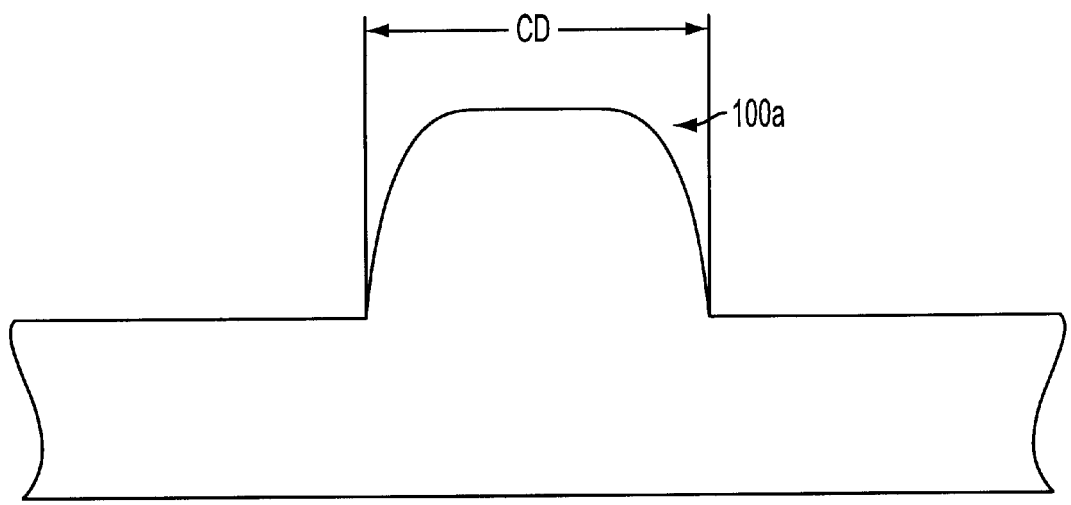
Figure 2:
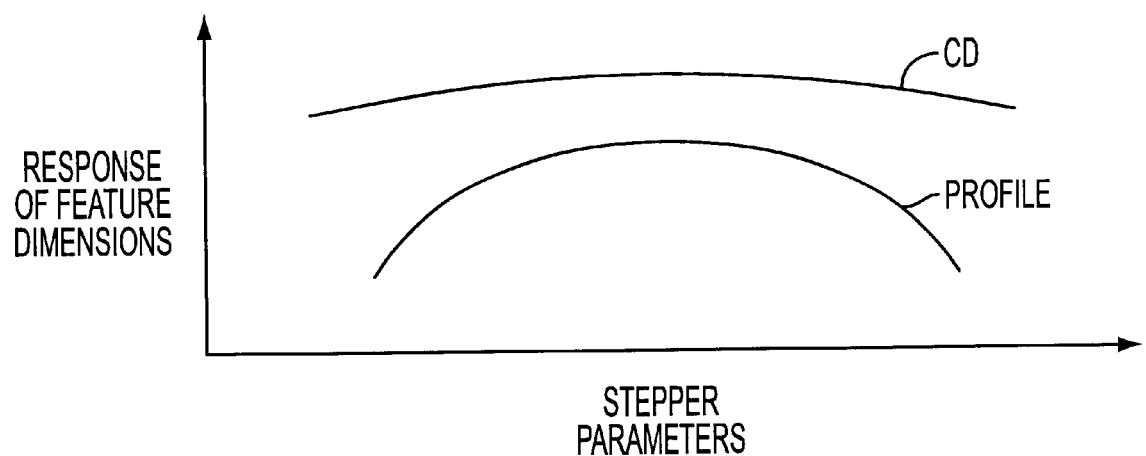
FIG. 2 is a graphical representation of the relationship between stepper parameters and changes in feature dimensions.

Conventional methodologies for in-process inspection of features formed on the surface of semiconductor wafers do not quickly and economically yield usable information regarding feature profiles. Furthermore, conventional inspection techniques are not capable of analyzing CD and/or profile deviations from design rules in sufficient detail to provide information leading to early positive identification of the source of the defect or dimensional variation. The present invention addresses and solves these problems by quickly and economically providing profile information without destroying the wafer under inspection, enabling ready identification of processes causing defects, and enabling early corrective action to be taken.

According to the methodology of the present invention, a "library" of reference waveforms, such as conventional SEM waveforms, is created by imaging a plurality of reference features formed, as on a test wafer, using the mask which will be used in producing the features to be inspected. Each of the reference features is formed using different process parameters, such as different stepper focus and exposure settings. After creating the reference SEM waveforms, the profile of each of the reference features is imaged, as by a cross-section FIB-SEM. Thus, each reference SEM waveform is associated with a known profile and known stepper settings. Subsequently, the reference waveform associated with the particular cross-section SEM waveform having optimal profile and/or other characteristics is chosen and identified as a "golden waveform".

A feature of unknown profile to be inspected is conventionally imaged with an SEM, and the resulting waveform is compared to the golden waveform. If the feature's waveform does not substantially match the golden waveform, it is compared to the reference feature waveforms to find the closest matching reference waveform. The profile and stepper settings of the matching reference waveform (which correspond to the profile and stepper settings of the feature under inspection) are then compared to those associated with the golden waveform to aid in identifying process problems (e.g., stepper defocusing, underexposure or overexposure). Thus, stepper focus and exposure settings of a feature under inspection are pinpointed, and its profile determined, by obtaining its SEM waveform and comparing the waveform to a library of reference feature waveforms, thereby enabling fast and economical identification of defects or variations from design standards as well as the cause of those defects.

In a preferred embodiment of the invention, the library of reference waveforms is formed as a focus exposure matrix ("FEM") on a test wafer, which is a conventional technique for obtaining the best exposure/focus combination when new masks are produced or after a change in the fabrication recipe; i.e., to optimize the process by finding the combination of stepper focus and exposure which results in the best resolution on the wafer, in keeping with the required CD. The FEM procedure typically comprises sequentially exposing a series of areas of the test wafer with the pattern of the mask, while exposure and focus values are incrementally changed from one exposure location to the next. Specifically, the test wafer is exposed in a stepper while the focus is varied along one axis and the exposure is varied along the other. Thus, a matrix of features is obtained on the exposed wafer, wherein each exposure site or die has a different focus-exposure setting.

Figure 3:
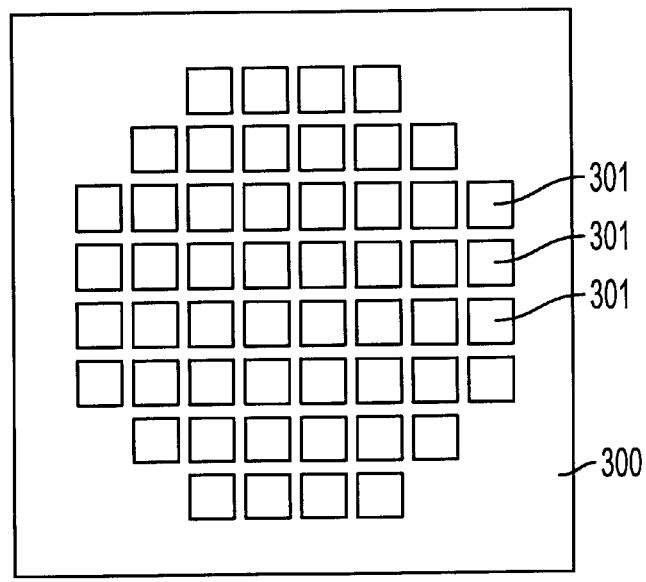
FIG. 3 illustrates a portion of a mask used in practicing the present invention.

FIG. 3 illustrates a portion of a typical photolithographic mask 300, illustrating a number of circuit patterns 301, shown schematically. In the illustrated mask, as would be used in a scanner, all the circuit patterns to be formed on a semiconductor wafer are shown; however, it is also customary to have only a few circuit patterns on a mask; e.g., from 1 to 9 patterns, in which case the mask can be used in a "step and scan" method of exposing the semiconductor wafer.

Figure 4:
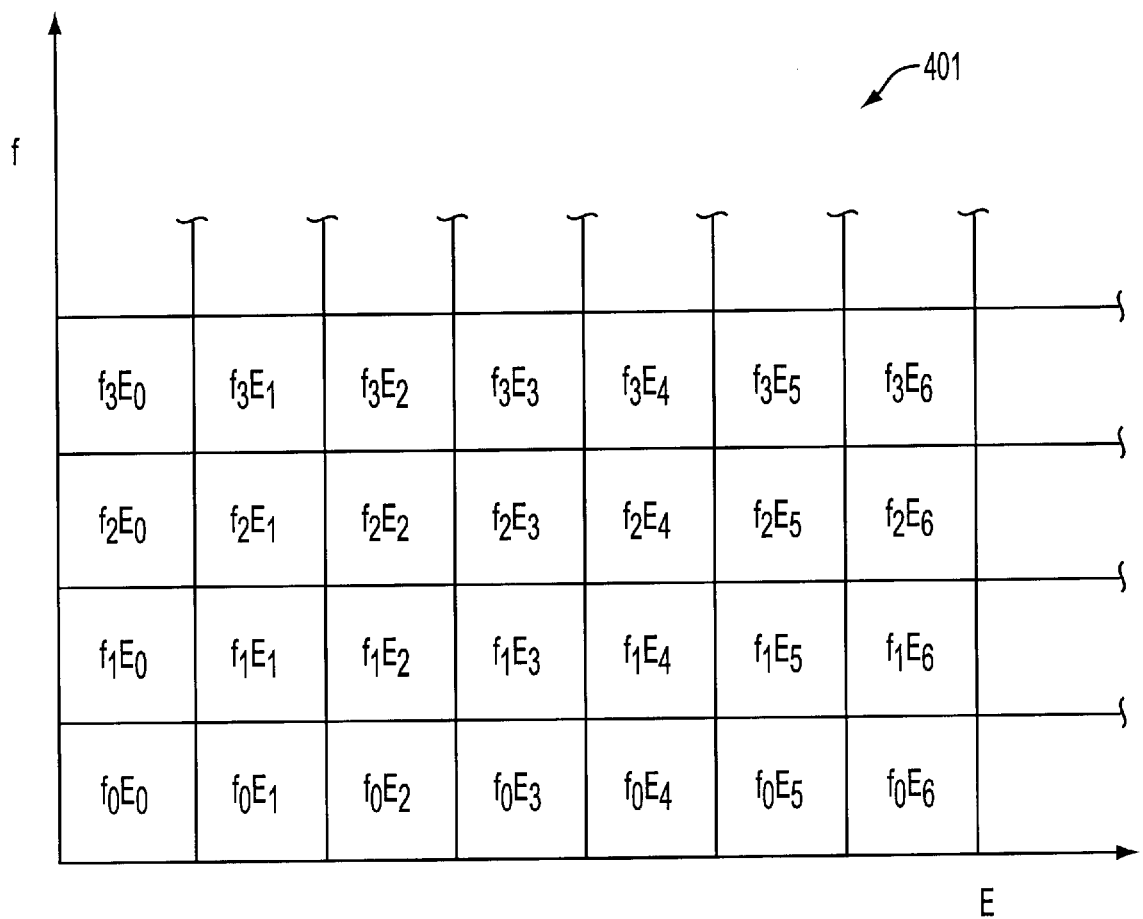
FIG. 4 illustrates a portion of a focus exposure matrix used in practicing an embodiment of the present invention.

FIG. 4 illustrates a portion of a focus-exposure matrix. The matrix 401 is formed by patterning the wafer surface using light or other radiation passing through the mask. A single wafer may include tens or hundreds of dies depending on die size, each of which corresponds to one the exposure areas shown in FIG. 4. For convenience, only a small number of the dies are illustrated. Each of the dies of the matrix has an incrementally different exposure E and/or was formed with an incrementally different focus f than any of the surrounding dies, as referenced by nomenclature $F_nE_m$ in the drawings. The focus is varied along one axis while the exposure is varied along the other axis in the formation of the matrix.

After exposure of the wafer, the individual exposure sites are developed and then examined with a conventional CD-SEM scan, and the resulting waveforms stored to obtain a reference waveform for each site. The exposure sites are then imaged with an atomic force microscope (AFM) or sectioned and imaged with a cross-section FIB-SEM to determine their respective profiles. An evaluation of the cross-sectional profile images is performed to determine the combination of focus and exposure settings which produces the best profile. The reference waveform (i.e., conventional SEM waveform) corresponding to the combination of stepper focus and exposure settings that produced the best profile is then designated as a golden waveform.

Figure 5:
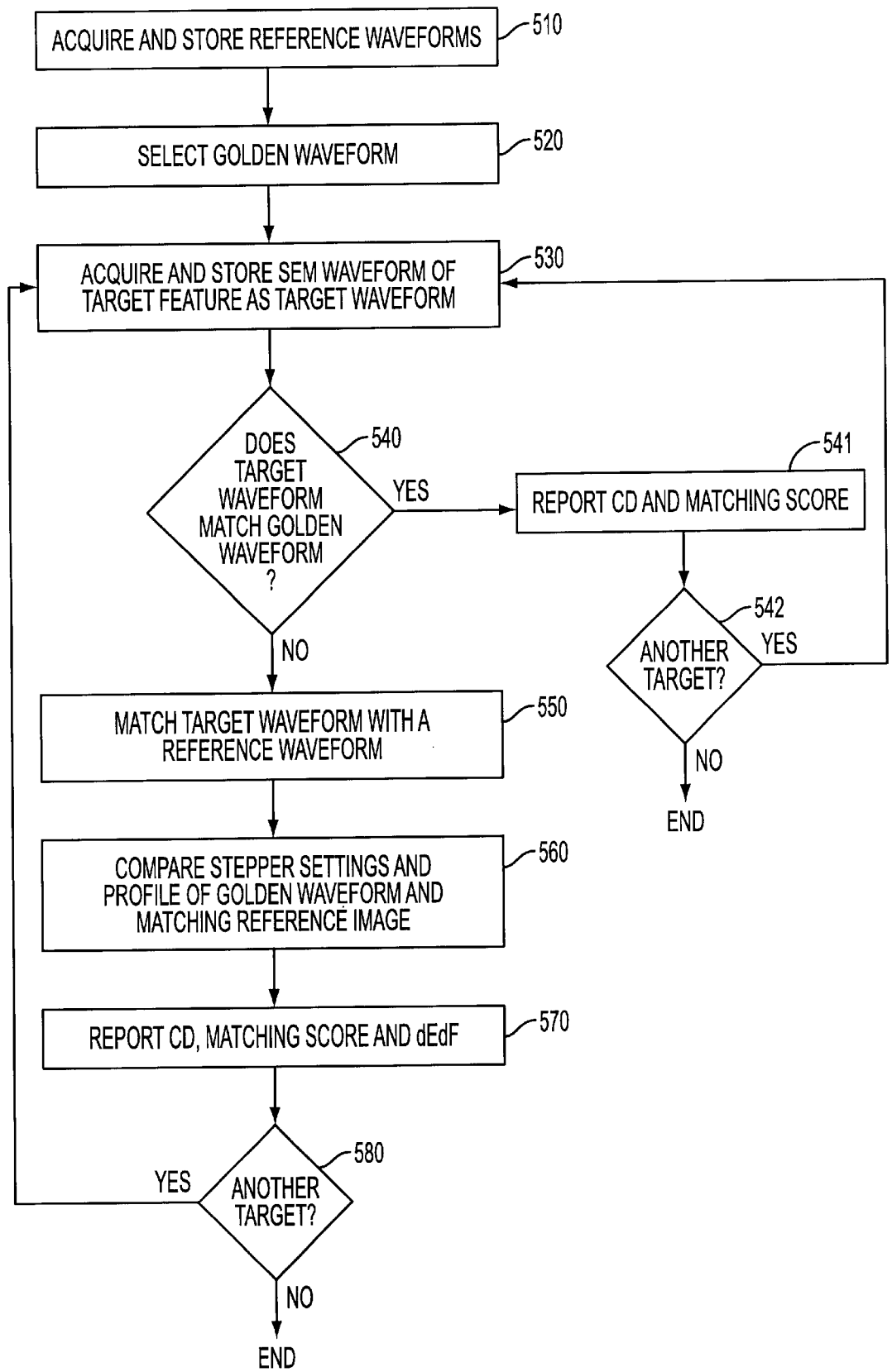
FIG. 5 is a flow chart illustrating sequential steps in a method according to an embodiment of the present invention.

FIG. 5 is a flow chart illustrating the major steps of inspecting a feature (hereinafter called a "target feature") formed with the mask on a semiconductor wafer according to the methodology of this embodiment of the invention. At step 510, the reference library is created, including reference waveforms in the form of SEM waveforms, and stored locally at the SEM inspection tool or in a computer software-implemented database system known as a "manufacturing execution system" (MES) conventionally used for storage of process information. The stepper settings and profile images associated with each of the reference waveforms can also be stored, if desired by the user. The reference library is created only once for each layer to be inspected; i.e., after a series of process steps creates a "critical layer" that the user determines must be inspected. The golden waveform is selected at step 520. All waveforms and data referred to in the present disclosure and claims are preferably electronically stored (such as on magnetic or optical recording media), and all disclosed image manipulation and analysis is preferably automatically performed electronically.

The target feature is imaged, as by CD-SEM, at step 530, and its waveform is stored as a target waveform. At step 540, the target waveform is compared to the golden waveform. If the target waveform and golden waveform match within predetermined limits, the CD of the target feature is reported, along with a "matching score" indicating the amount of deviation of the target waveform from the golden waveform (see step 541). The inspection then ends for the target feature, and the process is repeated from step 530, if required, for another target feature (see step 542).

If the target waveform does not match the golden waveform, the target waveform is compared to each of the reference waveforms in the library to identify the reference waveform most closely matching the target waveform (see step 550). The profile and stepper settings of the matching reference waveform are then reported, as they are considered to substantially correspond to the profile and stepper settings of the target feature. The reported stepper settings are compared with those associated with the golden waveform at step 560 to determine the difference dEdF between the settings which produced the golden waveform and those which produced the target feature; e.g., determine the difference between the focus setting associated with the golden waveform and the focus setting associated with the target feature, and determine the difference between the exposure setting associated with the golden waveform and the exposure setting associated with the target feature. The CD of the target feature is then reported at step 570, along with its matching score and dEdF, ending the inspection of the target feature, and the process is repeated from step 530, if required, for another target feature (see step 580).

Thus, the present methodology enables a determination of the location on FIG. 4's FEM of the target feature's stepper settings and their relative location with respect to those associated with the golden waveform. This indicates the amount of adjustment to the stepper that is required, as well as which particular adjustments (i.e., focus, exposure, or both) should be made.

To monitor more closely the effects of deviation from optimal process parameters, if an error is found in the target waveform (i.e., if the golden waveform is not the closest matching waveform to the target waveform), the profile of the target feature can be imaged, such as by AFM or cross-section FIB-SEM, and the image can be added to the reference library of profiles and be associated with the reference waveform which most closely matches the target waveform. Thus, the reference library can be augmented or updated with profiles of actual features of wafers under inspection, to give the user a more accurate view of the shape of the profiles of features under inspection.

In a further embodiment of the present invention, the user determines an acceptable deviation from the optimal process parameters, and an alarm is given if a target feature falls outside the acceptable deviation. For example, the user can select a threshold matching score, and if a feature's matching score indicates a greater deviation from the golden waveform than the threshold, an alarm is sounded. Alternatively, the user may select a range of acceptable differences dEdF between the stepper settings which produced the golden waveform and those which produced the target feature, and if dEdF of the target feature falls outside the selected range, an alarm is given. The alarm can also be given if the target feature matches a particular reference feature. In other words, the user can decide whether or not a target feature's position on the FEM of FIG. 4 is acceptable. In deciding a target feature's acceptability, the user can use the images of profiles of target features in the augmented reference library, as discussed above. For example, a series of target feature profile images may show the progression of profile degradation as the stepper goes out of focus, thereby assisting the user in determining when the alarm should be given.

Thus, the user can closely monitor the performance of a process or a machine. For example, the user can detect when a stepper's focus or exposure is drifting. Referring again to FIG. 4, if the optimal focus/exposure setting is $F_1E_2$, the user can specify that an alarm be given if the target feature's matching reference waveform is associated with $F_1E_5$, $F_1E_6$, etc., since this indicates that the stepper's exposure is drifting.

Figure 6A:
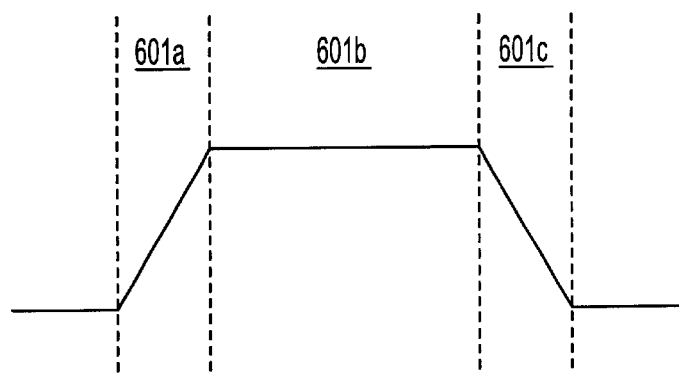
FIG. 6A is a view of a profile of a feature to be inspected using the methodology of the present invention.
Figure 6B:
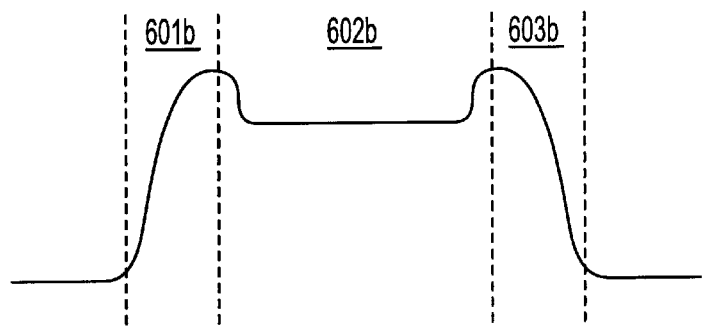
FIGS. 6B and 6C are graphical representations of waveforms used in practicing an embodiment of the present invention.
Figure 6C:
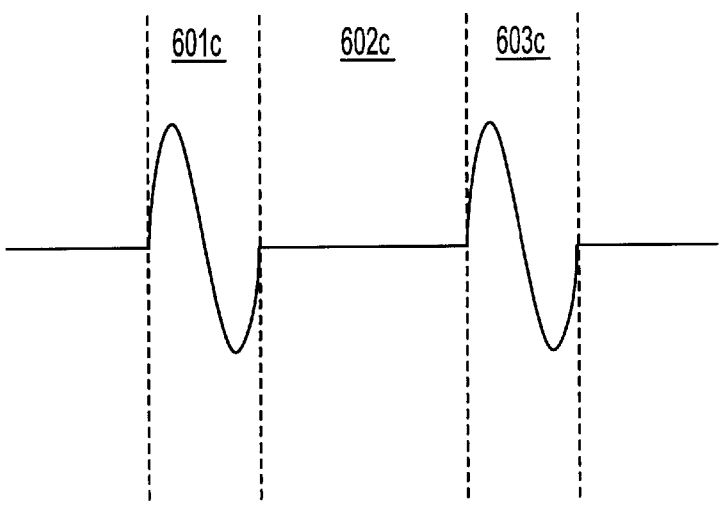

In another embodiment of the invention, the step of comparing the target waveform to the golden waveform (step 540) and the step of matching the target waveform to one of the reference waveforms (step 550) comprise comparing only a selected portion of the target waveform and the reference/golden waveforms which represents a significant feature of the profile under inspection. By analyzing only a portion of the waveforms containing the most pertinent information, processing time is reduced. FIG. 6A depicts a typical feature profile, FIG. 6B shows the corresponding SEM waveform of the feature of FIG. 6A, and FIG. 6C is a graphical representation of the first derivative of the SEM waveform of FIG. 6B. Since portions 601a and 603a are the most important areas of the feature profile to be inspected, and correspond to segments 601b and 603b of the SEM waveform in FIG. 6B and segments 601c and 603c of the first derivative shown in FIG. 6C, it is advantageous to match segments 601c or 603c of the first derivatives of the target and reference waveforms.

Figure 6D:
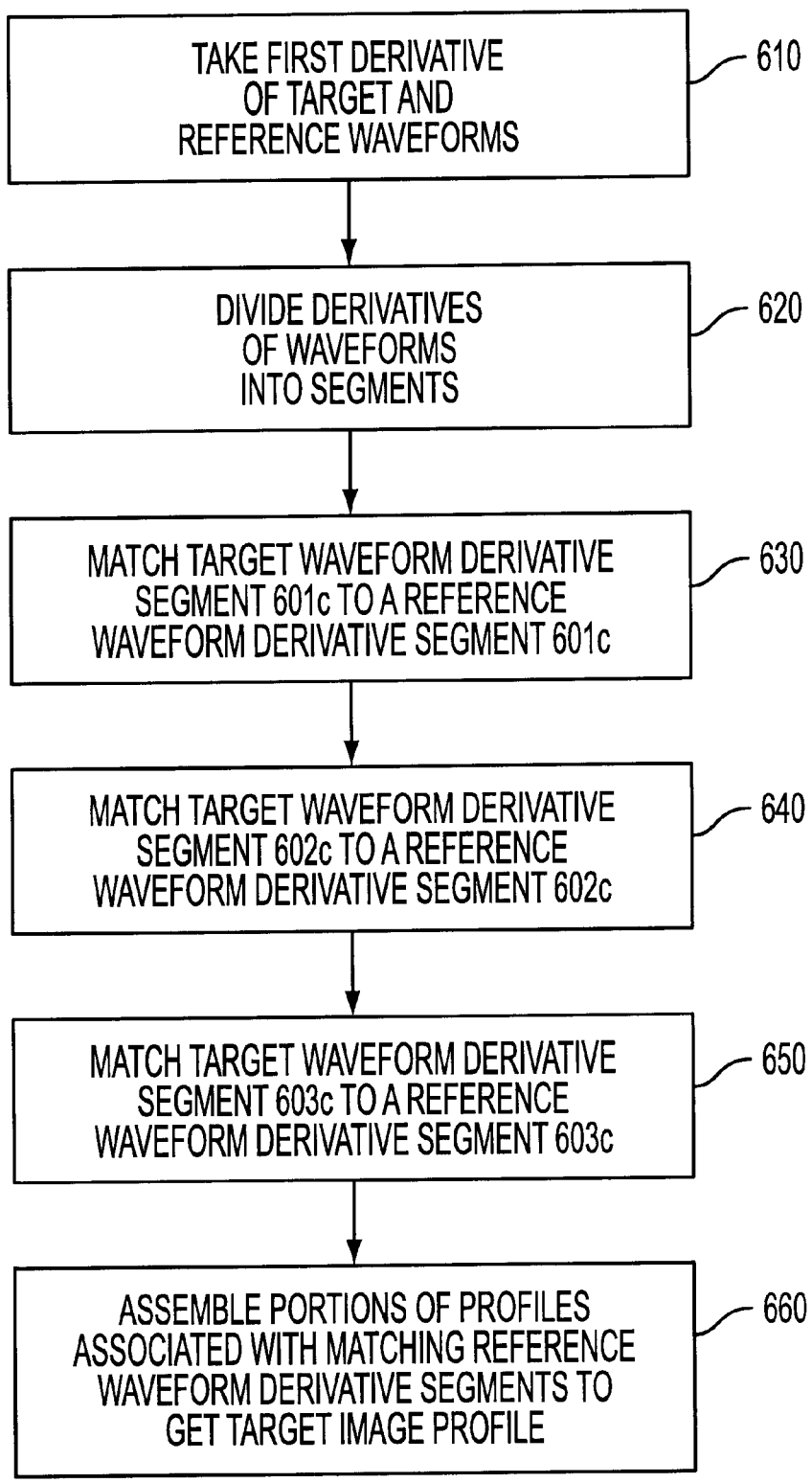
FIG. 6D is a flow chart illustrating sequential steps in a method according to an embodiment of the present invention.

In still another embodiment of the invention, as illustrated in the flow chart of FIG. 6D, if the target waveform does not match the golden waveform in step 540 of the flow chart of FIG. 5, the first derivative of the target and reference waveforms are taken (step 610), and divided into segments at step 620, such as segments 601c, 602c and 603c in FIG. 6C. Then, each of segments 601c, 602c and 603c of the derivative of the target waveform is separately matched to a corresponding segment of the derivative of a reference waveform (see steps 630, 640, 650), which is associated with a portion of a known profile (e.g., portion 601a, 602a, 603a of FIG. 6A). Thus, the profile of the target feature is predicted by assembling "building blocks" of matching segments (step 660). An examination of the predicted profile will indicate what part or parts of the profile deviate from design standards, and such information can be used by one skilled in the art to trace photolithographic processing problems, such as focus and exposure problems.

In a further embodiment of the present invention, the step of comparing the target waveform to the golden waveform (step 540) and the step of matching the target waveform to one of the reference waveforms (step 550) comprise employing an algorithm to "fit a curve" to the target and reference SEM waveforms such as depicted in FIG. 6B; that is, to obtain a mathematical function or "formula" representative of the shape of each of the waveforms. Then, corresponding significant elements of the mathematical functions representative of the target and reference waveforms are compared to determine which reference image most closely matches the target image. For example, if the target and reference waveforms are represented by the function y=F(x, a, b), the reference waveform whose values of x, a and b most closely match the x, a and b values of the target waveform is the reference waveform that most closely matches the target waveform.

In a still further embodiment of the present invention, the step of comparing the target waveform to the golden waveform (step 540) and the step of matching the target waveform to one of the reference waveforms (step 550) comprise using the target and reference waveforms to generate images of the target feature and the reference features, and then comparing the generated images. In other words, SEM waveforms as illustrated in FIG. 6B are manipulated using conventional computer graphics techniques to generate images as shown in FIG. 6A. The generated images are then matched, as by well-known pattern recognition techniques such as boundary analysis and grey-scale analysis, as described, for example, in copending U.S. patent application Ser. No. 09/111,454, filed Jul. 8, 1998, entitled "Automatic Defect Classification With Invariant Core Classes", the entire disclosure of which is hereby incorporated by reference.

In an alternative embodiment of the present invention, the target waveform is compared to the golden waveform at step 540 using any of the above-described techniques, the CD and matching score are reported, and the inspection procedure for that target feature ends. Thus, inspection time is reduced.

In another alternative embodiment of the present invention, a golden waveform is not selected. The target waveform is simply matched to a reference waveform and the CD and matching entry reported. Referring to FIG. 5, steps 520, 540 and 560 are eliminated: the library is created at step 510, the target waveform is acquired at step 530, the target waveform is matched to a reference waveform at step 550, and the CD and matching entry reported at step 570.

Figure 7:
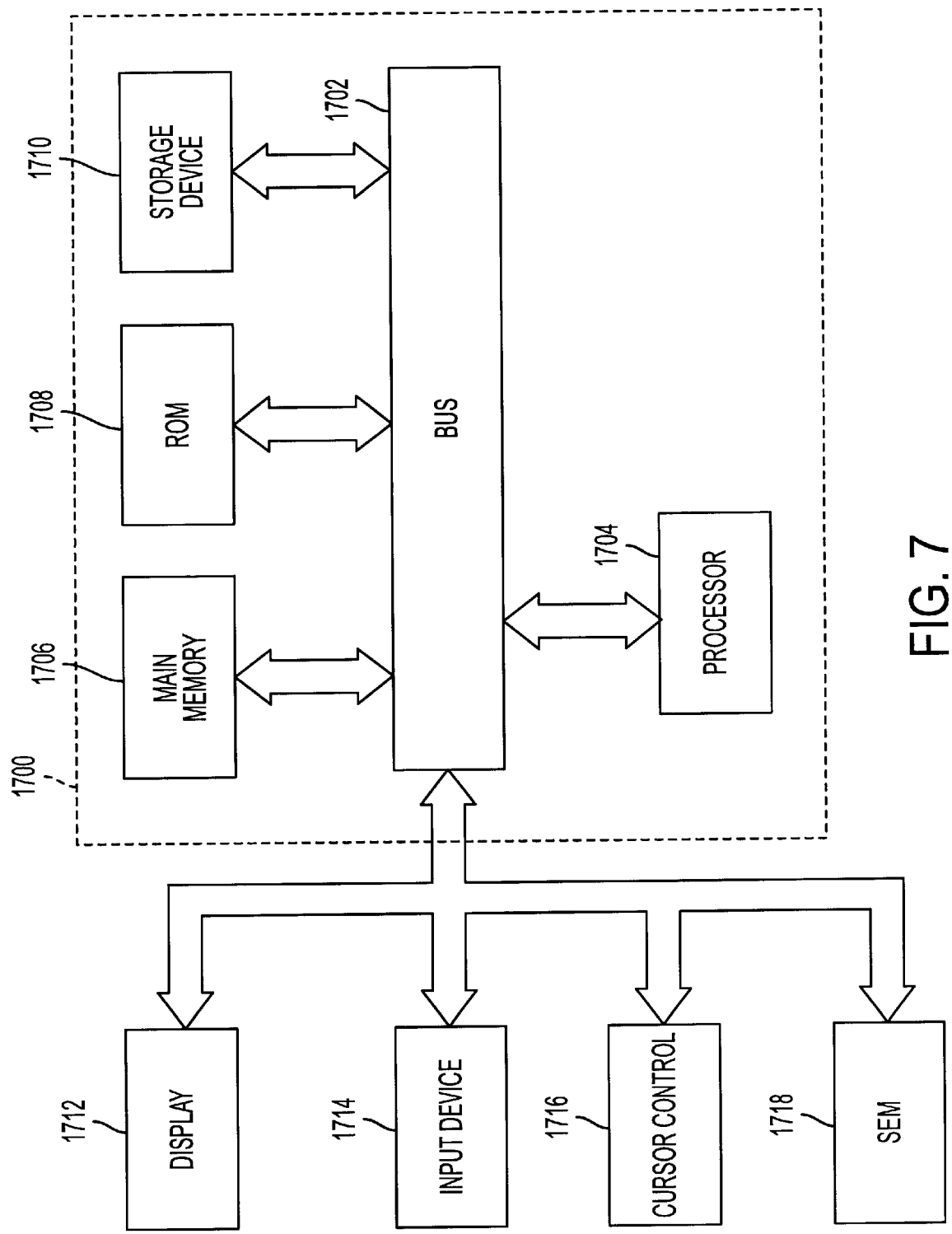
FIG. 7 is a block diagram that illustrates an embodiment of the invention.

FIG. 7 is a block diagram that illustrates an embodiment of the invention. A computer system 1700 includes a bus 1702 or other communication mechanism for communicating information, and a processor 1704 coupled with bus 1702 for processing information. Computer system 1700 also includes a main memory 1706, such as a random access memory (RAM) or other dynamic storage device, coupled to bus 1702 for storing information and instructions to be executed by processor 1704. Main memory 1706 also may be used for storing temporary variables or other intermediate information during execution of instructions to be executed by processor 1704. Computer system 1700 further includes a read only memory (ROM) 1708 or other static storage device coupled to bus 1702 for storing static information and instructions for processor 1704. A storage device 1710, such as a magnetic disk or optical disk, is provided and coupled to bus 1702 for storing information and instructions.

Computer system 1700 may be coupled via bus 1702 to a display 1712, such as a cathode ray tube (CRT), for displaying information to a computer user. An input device 1714, including alphanumeric and other keys, is coupled to bus 1702 for communicating information and command selections to processor 1704. Another type of user input device is cursor control 1716, such as a mouse, a trackball, or cursor direction keys for communicating direction information and command selections to processor 1704 and for controlling cursor movement on display 1712.

An SEM 1718 inputs data representative of features of a semiconductor wafer under inspection, as discussed above, to bus 1702. Such data may be stored in main memory 1706 and/or storage device 1710, and used by processor 1704 as it executes instructions. SEM 1718 may also receive instructions via bus 1702 from processor 1704.

The invention is related to the use of computer system 1700 for inspecting features formed on the surface of a semiconductor wafer. According to one embodiment of the invention, inspection of the surface of a semiconductor wafer is provided by computer system 1700 in response to processor 1704 executing one or more sequences of one or more instructions contained in main memory 1706. Such instructions may be read into main memory 1706 from another computer-readable medium, such as storage device 1710. Execution of the sequences of instructions contained in main memory 1706 causes processor 1704 to perform the process steps described above. One or more processors in a multi-processing arrangement may also be employed to execute the sequences of instructions contained in main memory 1706. In alternative embodiments, hard-wired circuitry may be used in place of or in combination with software instructions to implement the invention. Thus, embodiments of the invention are not limited to any specific combination of hardware circuitry and software. The programming of the apparatus is readily accomplished by one of ordinary skill in the art provided with the flow charts of FIG. 5 and FIG. 6D.

The term "computer-readable medium" as used herein refers to any medium that participates in providing instructions to processor 1704 for execution. Such a medium may take many forms, including but not limited to, non-volatile media, volatile media, and transmission media. Non-volatile media include, for example, optical or magnetic disks, such as storage device 1710. Volatile media include dynamic memory, such as main memory 1706. Transmission media include coaxial cable, copper wire and fiber optics, including the wires that comprise bus 1702. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, or any other medium from which a computer can read.

Various forms of computer-readable media may be involved in carrying out one or more sequences of one or more instructions to processor 104 for execution. For example, the instructions may initially be borne on a magnetic disk of a remote computer. The remote computer can load the instructions into its dynamic memory and send the instructions over a telephone line using a modem. A modem local to computer system 1700 can receive the data on the telephone line and use an infrared transmitter to convert the data to an infrared signal. An infrared detector coupled to bus 1702 can receive the data carried in the infrared signal and place the data on bus 1702. Bus 1702 carries the data to main memory 1706, from which processor 1704 retrieves and executes the instructions. The instructions received by main memory 1706 may optionally be stored on storage device 1710 either before or after execution by processor 1704.

The inventive semiconductor wafer inspection technique enables the profile of features formed on the surface of a wafer to be predicted by inspecting the feature using standard SEM imaging techniques, without damaging the wafer under inspection. It also pinpoints the stepper settings of the inspected feature, thereby facilitating investigation of the causes of feature defects or variations from optimal dimensions, enabling effective corrective action to be implemented. Thus, the present invention contributes to the maintenance of high production throughput. The inventive methodology determines a suspected defective feature's profile and stepper settings by comparing its SEM waveform with the waveforms of a library of reference features obtained by forming a pre-production FEM. Therefore, the present invention is especially useful during the start-up and ramp-up of a production line.

The present invention is applicable to the inspection of any semiconductor wafer, and is especially useful for in-process inspection of semiconductor wafers during manufacture of high density semiconductor devices with submicron design features.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A method of inspecting a target feature on a semiconductor wafer, which method comprises:

forming a plurality of comparable reference features on a reference semiconductor wafer, the reference features having a profile comparable to a profile of the target feature, each of the reference features respectively associated with a different known profile and stepper setting;

obtaining a reference waveform of each of the reference features;

selecting one of the reference waveforms as a golden waveform;

obtaining a target waveform of the target feature;

comparing the target waveform with the golden waveform;

identifying the reference waveform which most closely matches the target waveform to obtain the profile of the target feature and a target feature stepper setting; and determining the difference between the stepper setting associated with the golden waveform and the stepper setting associated with the target feature when the golden waveform is not the reference waveform that most closely matches the target waveform.

2. The method according to claim 1, comprising photolithographically forming each of the plurality of reference features and the target feature using a common mask.

3. The method according to claim 2, wherein the stepper setting comprises a focus setting and an exposure setting.

4. The method according to claim 3, comprising:

determining one of the stepper settings is an optimal stepper setting; and identifying the reference waveform associated with the optimal stepper setting as the golden waveform.

5. The method according to claim 3, comprising forming the plurality of reference features as a focus exposure matrix (FEM).

6. The method according to claim 5, comprising:

imaging the reference features to obtain the reference waveforms;

sectioning the reference features; and imaging cross-sections of the reference features to obtain the profile associated with each reference waveform.

7. The method according to claim 1, comprising obtaining the reference waveforms and the target waveform as SEM waveforms.

8. The method according to claim 7, wherein the step of comparing the target waveform and the golden waveform, and the step of identifying the reference waveform which most closely matches the target waveform, comprise comparing a selected portion of the target waveform to a corresponding selected portion of the reference waveforms.

9. The method according to claim 7, wherein the step of comparing the target waveform and the golden waveform, and the step of identifying the reference waveform which most closely matches the target waveform, comprise:

obtaining a first derivative of the target waveform and the reference waveforms; and comparing a selected portion of the derivative of the target waveform to a corresponding selected portion of the derivatives of the reference waveforms.

10. The method according to claim 7, wherein the step of identifying the reference waveform that most closely matches the target waveform comprises:

obtaining a first derivative of the target waveform and the reference waveforms;

dividing the first derivative of the target waveform and the derivatives of the reference waveforms into at least two segments;

separately comparing corresponding segments of the derivatives of the target waveform and the reference waveforms to identify which segments of the derivatives of the reference waveforms most closely match the corresponding segments of the derivative of the target waveform; and assembling the profiles associated with the matching segments of the derivatives of the reference waveforms to predict the profile of the target feature.

11. The method according to claim 7, wherein the steps of comparing the target waveform with the golden waveform and identifying that one of the reference waveforms that most closely matches the target waveform comprise:

obtaining a mathematical function representative of the shape of the target waveform and the reference waveforms; and comparing a selected element of the mathematical function representative of the shape of the target waveform to a corresponding selected element of the mathematical functions representative of the shapes of the reference waveforms.

12. The method according to claim 1, wherein the steps of comparing the target waveform with the golden waveform and identifying that one of the reference waveforms that most closely matches the target waveform comprise:

generating images of the target feature and the reference features based on the target waveform and the reference waveforms; and performing a pattern recognition process.

13. The method according to claim 1, further comprising determining a matching score indicating the amount of deviation of the target waveform from the golden waveform when the golden waveform is the reference waveform that most closely matches the target waveform.

14. The method according to claim 1, further comprising determining a matching score indicating the amount of deviation of the target waveform from the golden waveform when the golden waveform is not the reference waveform that most closely matches the target waveform.

15. The method according to claim 3, wherein the step of determining the difference between the stepper setting associated with the golden waveform and the stepper setting associated with the target feature comprises:

determining the difference between the focus setting associated with the golden waveform and the focus setting associated with the target feature; and determining the difference between the exposure setting associated with the golden waveform and the exposure setting associated with the target feature.

16. A method of inspecting a target feature on a semiconductor wafer, which method comprises:

forming a plurality of comparable reference features on a reference semiconductor wafer, the reference features having a profile comparable to a profile of the target feature, each of the reference features respectively associated with a different known profile and stepper setting;

obtaining a reference waveform of each of the reference features;

selecting one of the reference waveforms as a golden waveform;

obtaining a target waveform of the target feature;

comparing the target waveform with the golden waveform; and determining a matching score indicating the amount of deviation of the target waveform from the golden waveform.

17. A computer-readable medium bearing instructions for inspecting a target feature on a semiconductor wafer, said instructions, when executed, being arranged to cause one or more processors to perform the steps of:

receiving a waveform corresponding to the target feature;

receiving a plurality of reference waveforms corresponding to a plurality of comparable reference features on a reference semiconductor wafer, the reference features having a profile comparable to a profile of the target feature, each of the reference features respectively associated with a different known profile and stepper setting;

receiving one of the reference waveforms as a golden waveform;

comparing the target waveform and the golden waveform;

identifying the reference waveform which most closely matches the target waveform to obtain the profile of the target feature and a target feature stepper setting; and determining the difference between the stepper setting associated with the golden waveform and the stepper setting associated with the target feature when the golden waveform is not the reference waveform that most closely matches the target waveform.

18. The computer-readable medium according to claim 17, wherein the instructions, when executed, are arranged to cause the one or more processors to receive the target and reference waveforms as SEM waveforms.

19. The computer-readable medium according to claim 18, wherein the instructions, when executed, are arranged to cause the one or more processors to perform the step of comparing the target waveform and the golden waveform, and the step of identifying the reference waveform which most closely matches the target waveform, by comparing a selected portion of the target waveform to a corresponding selected portion of the reference waveforms.

20. The computer-readable medium according to claim 18, wherein the instructions, when executed, are arranged to cause the one or more processors to perform the step of comparing the target waveform and the golden waveform, and the step of identifying the reference waveform which most closely matches the target waveform, by:

obtaining a first derivative of the target waveform and the reference waveforms; and comparing a selected portion of the derivative of the target waveform to a corresponding selected portion of the derivatives of the reference waveforms.

21. The computer-readable medium according to claim 18, wherein the instructions, when executed, are arranged to cause the one or more processors to perform the step of identifying the reference waveform that most closely matches the target waveform by:

obtaining a first derivative of the target waveform and the reference waveforms;

dividing the first derivative of the target waveform and the derivatives of the reference waveforms into at least two segments; and separately comparing corresponding segments of the derivatives of the target waveform and the reference waveforms to identify which segments of the derivatives of the reference waveforms most closely match the corresponding segments of the derivative of the target waveform; and assembling the profiles associated with the matching segments of the derivatives of the reference waveforms to produce a predicted profile of the target feature.

22. The computer-readable medium according to claim 18, wherein the instructions, when executed, are arranged to cause the one or more processors to perform the step of comparing the target waveform and the golden waveform, and the step of identifying the reference waveform that most closely matches the target waveform, by:

obtaining a mathematical function representative of the shape of the target waveform and the reference waveforms; and comparing a selected element of the mathematical function representative of the shape of the target waveform to a corresponding selected element of the mathematical functions representative of the shapes of the reference waveforms.

23. The computer-readable medium according to claim 18, wherein the instructions, when executed, are arranged to cause the one or more processors to perform the step of comparing the target waveform and the golden waveform, and the step of identifying the reference waveform that most closely matches the target waveform, by:

generating images of the target feature and the reference features based on the target waveform and the reference waveforms; and performing a pattern recognition process.

24. The computer-readable medium according to claim 17, wherein the instructions, when executed, are arranged to cause the one or more processors to receive the plurality of reference images as a focus exposure matrix (FEM).

25. An apparatus for inspecting a target feature on a semiconductor wafer, comprising:

an imager to produce a target waveform corresponding to the target feature;

a storage medium that stores:

the target waveform; and a plurality of reference waveforms corresponding to a plurality of comparable reference features on a reference semiconductor wafer, the reference features having a profile comparable to a profile of the target feature, each of the reference features respectively associated with a different known profile and stepper setting;

a processor configured to recognize one of the reference waveforms as a golden waveform; and a comparator that compares the target waveform and the golden waveform, and compares the target waveform and the reference waveforms;

wherein the processor is further configured to identify the reference waveform which most closely matches the target waveform to obtain the profile of the target feature and a target feature stepper setting, and to determine the difference between the stepper setting associated with the golden waveform and the stepper setting associated with the target feature when the golden waveform is not the reference waveform that most closely matches the target waveform.

26. The apparatus of claim 25, wherein the imager is a scanning electron microscope (SEM).

27. The apparatus of claim 25, wherein the storage medium is a digital storage device.

28. The apparatus of claim 25, wherein the processor is further configured to obtain a first derivative of the target waveform and the reference waveforms; and wherein the comparator compares a selected portion of the derivative of the target waveform to a corresponding selected portion of the derivatives of the reference waveforms.

29. The apparatus of claim 25, wherein the processor is further configured to obtain a first derivative of the target waveform and the reference waveforms, and to divide the first derivative of the target waveform and the derivatives of the reference waveforms into at least two segments;

wherein the comparator separately compares corresponding segments of the derivatives of the target waveform and the reference waveforms; and wherein the processor is further configured to identify which segments of the derivatives of the reference waveforms most closely match the corresponding segments of the derivative of the target waveform to assemble the profiles associated with the matching segments of the derivatives of the reference waveforms to produce a predicted profile of the target feature.

30. The apparatus of claim 25, wherein the processor is further configured to obtain a mathematical function representative of the shape of the target waveform and the reference waveforms; and wherein the comparator compares a selected element of the mathematical function representative of the shape of the target waveform to a corresponding selected element of the mathematical functions representative of the shapes of the reference waveforms.

31. The apparatus of claim 25, wherein the processor is further configured to generate images of the target feature and the reference features based on the target waveform and the reference waveforms; and wherein the comparator performs a pattern recognition process.

* * * * *